US008703495B2

(12) United States Patent
Young et al.

(10) Patent No.: US 8,703,495 B2
(45) Date of Patent: Apr. 22, 2014

(54) BLOOD COAGULATION DETECTION DEVICE AND METHOD

(75) Inventors: Kung-Chia Young, Tainan (TW); Song-Jeng Huang, Chiayi County (TW); Chin-Lung Yang, Tainan (TW)

(73) Assignee: National Cheng Kung University, Tainan (TW)

( * ) Notice: Subject to any disclaimer, the term of this patent is extended or adjusted under 35 U.S.C. 154(b) by 39 days.

(21) Appl. No.: 13/542,725

(22) Filed: Jul. 6, 2012

(65) Prior Publication Data

US 2013/0171736 A1 Jul. 4, 2013

(30) Foreign Application Priority Data

Jan. 2, 2012 (TW) .............................. 101100100 A

(51) Int. Cl.
*G01N 33/86* (2006.01)
*G01N 33/48* (2006.01)
*G01N 21/01* (2006.01)
*G01N 21/47* (2006.01)

(52) U.S. Cl.
USPC .................. 436/69; 436/63; 436/164; 422/73; 422/82.05; 422/82.09; 600/369; 73/64.41; 73/64.43

(58) Field of Classification Search
USPC ............. 436/63, 69, 149, 150, 164, 165, 180; 422/400, 401, 402, 403, 68.1, 73, 422/82.01, 82.02, 82.05, 82.09, 502; 435/13, 29; 600/369; 73/64.41, 64.43
See application file for complete search history.

(56) References Cited

U.S. PATENT DOCUMENTS

| 3,591,801 | A | * | 7/1971 | Watson | ........................ 250/373 |
| 4,217,107 | A | * | 8/1980 | Saito et al. | ...................... 436/69 |
| 4,454,752 | A | * | 6/1984 | Scordato | ...................... 73/64.43 |
| 4,951,680 | A | * | 8/1990 | Kirk et al. | ..................... 600/511 |
| 2006/0110283 | A1 | * | 5/2006 | Fish | ............................... 422/52 |

OTHER PUBLICATIONS

Yan-Chao Chiou et al., "Portable Blood Coagulation Detectors Using Optical Sensors", Annual Symposium on Biomedical Engineering and Technology, Aug. 19-20, 2011,Taiwan.
Yen-Chao Chiou et al., "Portable Optical-based Blood Coagulation Detectors", Symposium on Engineering, Medicine and Biology Applications, Jul. 8-10, 2011, Kaohsiung, Taiwan.
Cheng-Wei Chou et al., "Testing of Whole Blood Prothrombin Time with a Novel Portable Optical-Based Coagulation Detector", The 10th Chinese Laboratory Medicine Conference, Translational Medicine, Nov. 4-7, 2011, Taipei Taiwan.

* cited by examiner

*Primary Examiner* — Maureen Wallenhorst
(74) *Attorney, Agent, or Firm* — Bacon & Thomas, PLLC

(57) ABSTRACT

A blood coagulation detection device includes a micro channel unit, an optical signal unit, an opto-electronic conversion circuit, an amplifier circuit, and a filter circuit. The micro channel unit has a sample detection area. The optical signal unit transmits a reference light to the micro channel unit so as to form a message light. The opto-electronic conversion circuit receives the message light and converts the message light into an electrical signal. The amplifier circuit is electrically connected to the opto-electronic conversion circuit for amplifying the electrical signal. The filter circuit is electrically connected to the amplifier circuit for filtering the amplified electrical signal.

20 Claims, 5 Drawing Sheets

BLOOD COAGULATION DETECTION DEVICE AND METHOD

CROSS REFERENCE TO RELATED APPLICATION

This application claims the benefits of the Taiwan Patent Application Serial Number 101100100, filed on Jan. 2, 2012, the subject matter of which is incorporated herein by reference.

BACKGROUND OF THE INVENTION

1. Field of the Invention

The present invention relates to the technical field of blood coagulation detection and, more particularly, to a blood coagulation detection device and method.

2. Description of Related Art

Generally, blood coagulation time is an index for practically detecting whether the function of human body blood is normal or not. The blood coagulation effect is a series of avalanched reactions generated by activating a plurality of blood coagulation factors, so as to make the blood become blood clots, thereby achieving the final effect of stopping bleeding.

The blood coagulation factor is synthesized by the liver of human body. Therefore, when the liver function is lowered, the blood coagulation time is also prolonged. Thus, the blood coagulation time can be used as index for liver function. In addition, the patient who takes anticoagulant has to regularly perform blood coagulation detection for a long term, so as to monitor medicine-taking dosage for avoiding spontaneous bleeding. As a result, the detection of blood coagulation time is an important reference for diagnosing the lack of vitamin K and various liver troubles, and monitoring the patient who takes orally the anticoagulant.

In modern society, it is common for people to suffer from the diseases such as high blood pressure and cerebrovascular disease. In curing these diseases, medicines, for example aspirin, are typically required to be taken. However, these medicines may cause negative side effect, for example, resulting in that the blood coagulation time for those patients who take the medicines becomes longer. With the side effect of prolonging the blood coagulation time, if a patient is injured and has internal organs bleeding for certain reasons, the patient may lose a great amount of blood or even be in danger of life.

Therefore, it is important to monitor the blood coagulation time for patients. In the early stage, the detection of the blood coagulation time is done in a hospital, and the detection process is extremely time-consuming. In addition, the existing method for detecting the blood coagulation time is employed to first apply centrifugal force to the blood of the patient for separating the plasma, and then dilute the plasma for proceeding with blood coagulation detector analysis. However, because the volume of the centrifuge machine is relatively large, it is impossible for patients to carry the machine. Furthermore, the blood sample has been processed by centrifugal force, and thus it cannot represent the actual physiology situation of a patient.

Due to the aforementioned reasons, the detection of blood coagulation time is not popular. Therefore, if a blood coagulation detection device, which is easy to operate and convenient to carry and directly uses the whole blood sample for detection, can be developed, the detection of blood coagulation time can be made to become popular, so that most patients or persons can detect the blood coagulation time by themselves via the developed blood coagulation detection device.

SUMMARY OF THE INVENTION

One object of the present invention is to provide a blood coagulation detection device, which can directly use whole blood for detection and which can be manufactured at a low cost.

Another object of the present invention is to provide a blood coagulation detection method, which can easily and conveniently detect the blood coagulation time, so that a user can detect the blood coagulation time by himself/herself at anywhere.

In one aspect of the present invention, there is provided a blood coagulation detection device, which comprises: a micro channel unit having a sample detection area; an optical signal unit for transmitting a reference light to the micro channel unit so as to form a message light; an opto-electronic conversion circuit for receiving the message light and converting the message light into an electrical signal; an amplifier circuit electrically connected to the opto-electronic conversion circuit for amplifying the electrical signal; and a filter circuit electrically connected to the amplifier circuit for filtering the amplified electrical signal.

In another aspect of the present invention, there is provided a blood coagulation detection method, which comprises: providing a micro channel unit, which has a sample detection area in which a blood sample is placed; providing an optical signal unit, which emits a reference light to the blood sample for forming a message light; providing an opto-electronic conversion circuit, which receives the message light and converts the message light into an electrical signal; providing an amplifier circuit, which amplifies the electrical signal; and providing a filter circuit, which performs a filtering to the electrical signal that has been amplified by the amplifier circuit.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
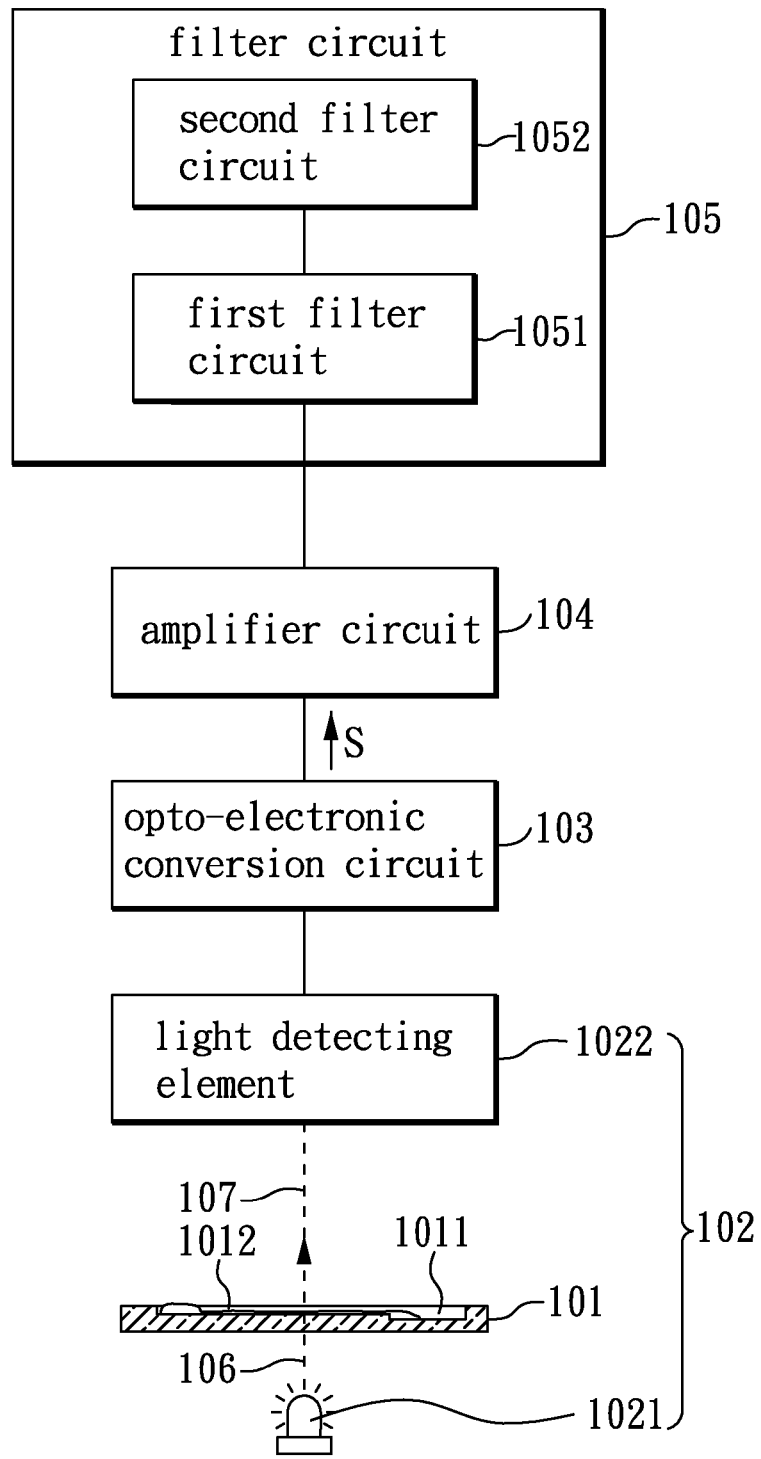
FIG. 1 shows a blood coagulation detection device in accordance with a preferred embodiment of the present invention.

With reference to FIG. 1, there is shown a blood coagulation detection device in accordance with a preferred embodiment of the present invention. As shown, the blood coagulation detection device includes: a micro channel unit 101, an optical signal unit 102, an opto-electronic conversion circuit 103, an amplifier circuit 104, and a filter circuit 105. The micro channel unit 101 has a sample detection area 1011. The optical signal unit 102 includes a light emitting element 1021 and a light detecting element 1022. The light emitting element 1021 of the optical signal unit 102 emits a reference light 106 to the micro channel unit 101 thereby forming a message light 107 for being collected by the light detecting element 1022.

Furthermore, the light detecting element 1022 transmits the collected message light 107 to the opto-electronic conversion circuit 103. The opto-electronic conversion circuit 103 converts the message light 107 into an electrical signal S. The amplifier circuit 104 is electrically connected to the opto-electronic conversion circuit 103 for amplifying the electrical signal S. In addition, the filter circuit 105 is electrically connected to the amplifier circuit 104, and the filter circuit 105 performs a filtering to the amplified electrical signal S.

It is noted that, in the optical signal unit 102 of the blood coagulation detection device in accordance with the present invention, the light emitting element 1021 is a light emitting diode for emitting the aforementioned reference light 106, and the light detecting element 1022 is a photoresistor for sensing the message light 107 converted from the reference light 106 that passes through the micro channel unit 101.

In addition, the sample detection area 1011 of the micro channel unit 101 is provided to receive a blood sample. In this preferred embodiment, a whole blood sample is directly taken as the blood sample. When the blood starts to coagulate, the prothrombin in the blood begins to combine with the fibrinogen in the plasma for forming fibrin, and lots of blood platelets begin to be transformed into fibers intersected and overlapped with each other, resulting in a turbid state that lowers the light penetrability.

In view of the foregoing, it is known that the internal character of the blood will change after being coagulated, so that the reference light 106 passing through the blood sample will have a change in light penetrability, thereby forming the message light 107. Accordingly, by analyzing the message light 7, it is able to know the blood coagulation status.

It is further noted that, because the blood has a maximum absorption degree for the wavelengths of 540 nanometers and 570 nanometers and this wavelength range is overlapped with the wavelength of green light, the light emitting diode of the blood coagulation detection device in accordance with the present invention is preferred to be a green light emitting diode.

In addition, the light detecting element 1022 is preferred to be a photoresistor. When the reference light 106 passes through the blood sample for forming the message light 107, the light detecting element 1022 is provided to receive the message light 107. Next, the opto-electronic conversion circuit 103 converts the message light 107 into an electrical signal S, wherein the opto-electronic conversion circuit 103 is a bridge circuit. It is noted that any bridge circuit capable of converting the signal of photoresistor into electrical signal is suitable for use in the present invention, for example, a Wheatstone bridge or a Kelvin bridge. Preferably, in the blood coagulation detection device in accordance with the present invention, the bridge circuit is a Wheatstone bridge.

The message light is converted by the photoresistor into a resistance value, and the Wheatstone bridge transforms the resistance value into a voltage change for being signal-processed by the amplifier circuit 104. In this embodiment, the amplifier circuit 104 is preferably an instrumentation amplifier, which not only provides the effect of signal amplification but also reduces the common mode noises. Because the change of the light passing through blood is extremely small, the signal strength of the message light 107 is also very low. Thus, the use of instrumentation amplifier is able to increase the accuracy of the blood coagulation detection device in accordance with the present invention.

Then, the amplified electrical signal is applied to the filter circuit 105 for performing a filtering process, wherein the filter circuit 105 includes a first filter circuit 1051 and a second filter circuit 1052. The first filter circuit 1051 is electrically connected to the amplifier circuit 104, and the second filter circuit 1052 is electrically connected to the first filter circuit 1051.

Figure 2:
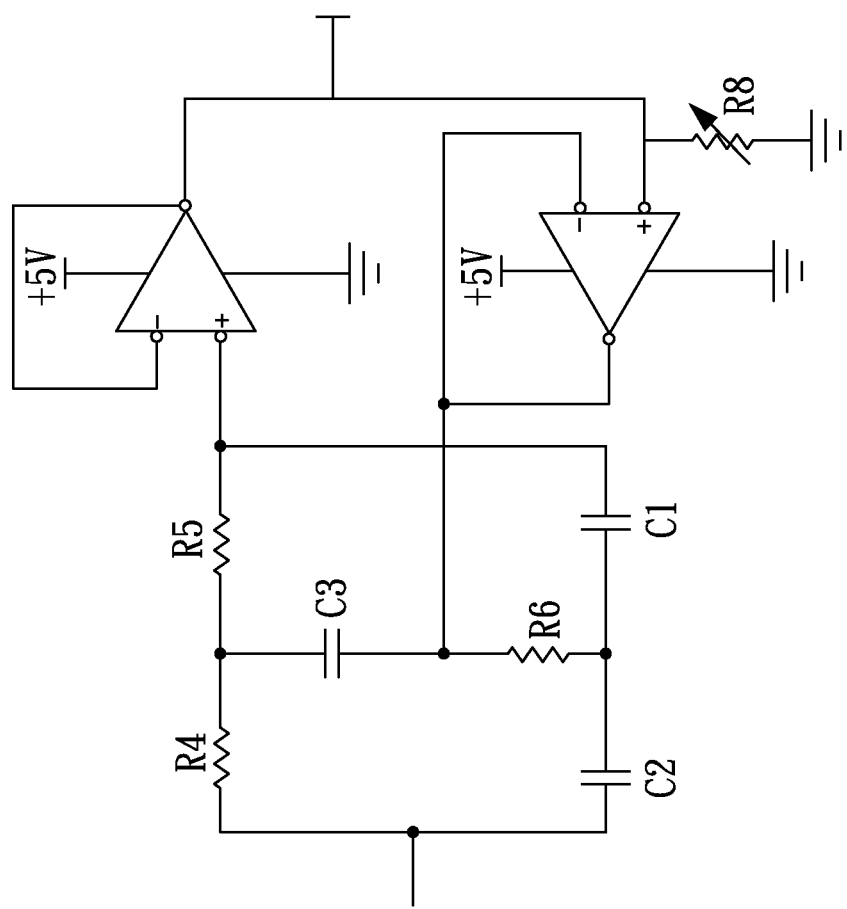
FIG. 2 shows a notch filter used in the blood coagulation detection device of the present invention.

It is further noted that, in the blood coagulation detection device of the present invention, the first filter circuit 1051 is preferably a notch filter, which can eliminate the noises caused by power supply or background. As shown in FIG. 2, there is shown a circuit schematic of the notch filter, in which the central frequency of the notch filter is set to be 60 Hz so that the noises at 60 Hz can be surely filtered out. After this filtering, the second filter circuit 1052 further performs a filtering.

Figure 3:
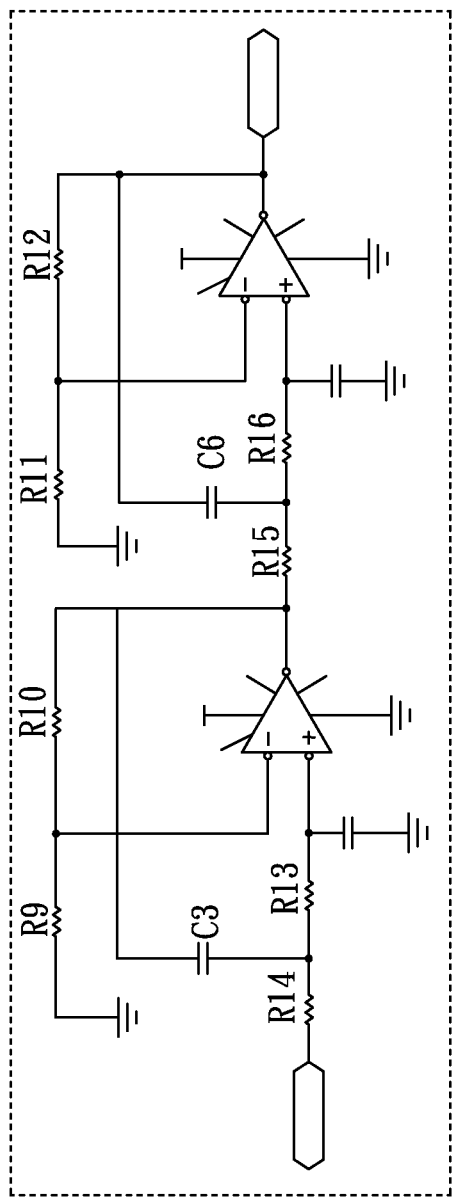
FIG. 3 shows a Butterworth filter used in the blood coagulation detection device of the present invention.

The second filtering circuit 1052 is a fourth-order low pass filter. In this embodiment, the fourth-order low pass filter is preferably a Butterworth filter. As shown in FIG. 3, there is shown a Butterworth filter used in the blood coagulation detection device of the present invention, wherein such a low pass filter of Butterworth architecture can further filter out other interfered noises so that the filtered signal can be smoother for output.

After analysis, in the blood coagulation detection device of the present invention, the frequency component of 25 Hz or above is deemed to be noise, and thus the second filter circuit 1052 has to completely filter out the frequency component of 25 Hz or above. Therefore, in FIG. 3, each of the resistors R13, R14, R15 and R16 is selected to have a resistance of 63 KΩ, and each of the capacitors C3, C4, C5 and C6 is selected to have a capacitance of 100 nF. As a result, the desired low pass filter can be achieved.

Figure 4:
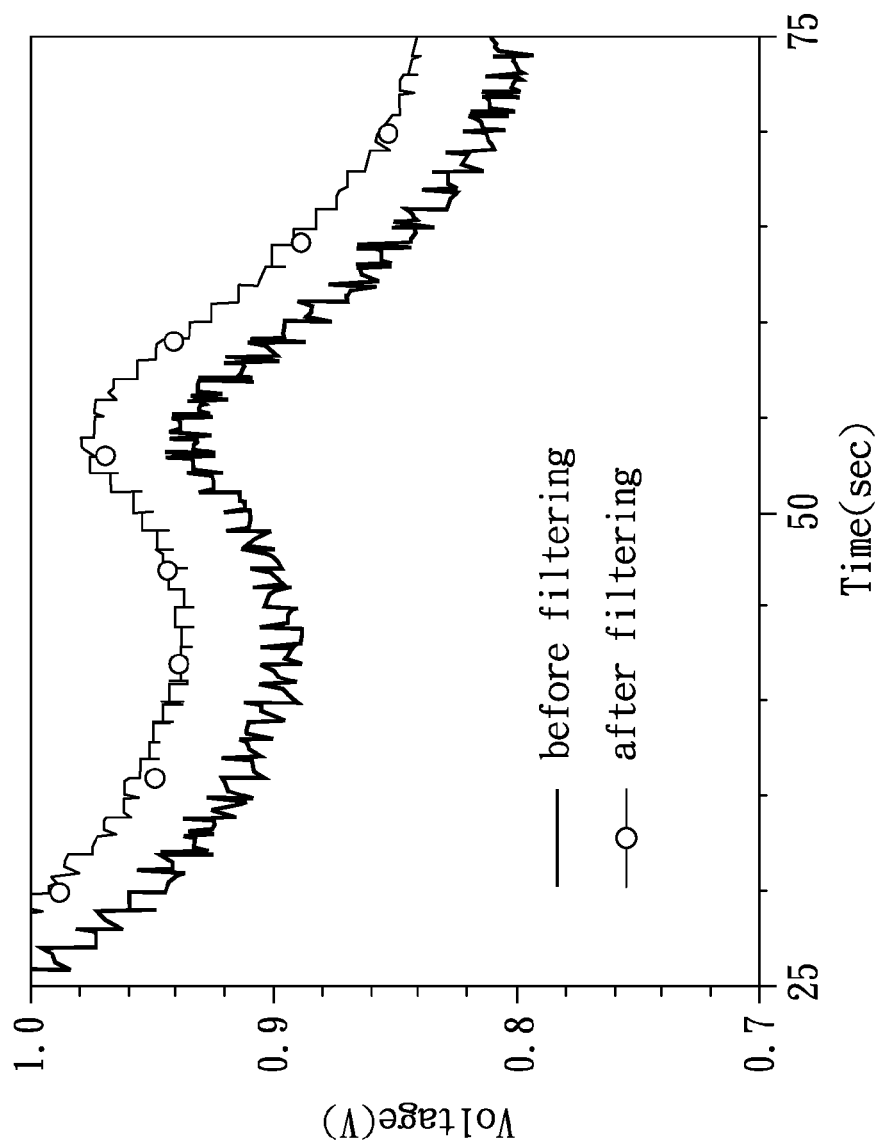
FIG. 4 shows a blood coagulation signal drawing of voltage vs. time before filtering and after filtering.

In addition, the cut-off frequency of the Butterworth filter is in the range of 20 Hz to 30 Hz. With reference to FIG. 4, there is shown a blood coagulation signal drawing of voltage vs. time before filtering and after filtering. As shown in FIG. 4, high-frequency noise is surely filtered out after filtering, so that the filtered signal becomes clear.

Preferably, the micro channel unit 101 further includes a micro channel 1012. The micro channel 1012 is connected to the sample detection area. In addition, the blood coagulation detection device of the present invention may further include a non-transparent unit (not shown), such as a mask body, which at least covers the micro channel unit 101 or simultaneously covers the micro channel unit 101 and the optical signal unit, wherein the non-transparent unit is made of acrylic material.

It is further noted that the blood coagulation detection device of the present invention may also include a transmitting element for transmitting signals obtained by the blood coagulation detection device to a back-end computer system for performing a further signal processing, analysis or storage. In this embodiment, the transmitting element is a wireless transmitting element, such as a Bluetooth transmitting element. In addition, the computer system can be a personal computer, a PDA (Personal Digital Assistant), or a smart phone.

Figure 5:
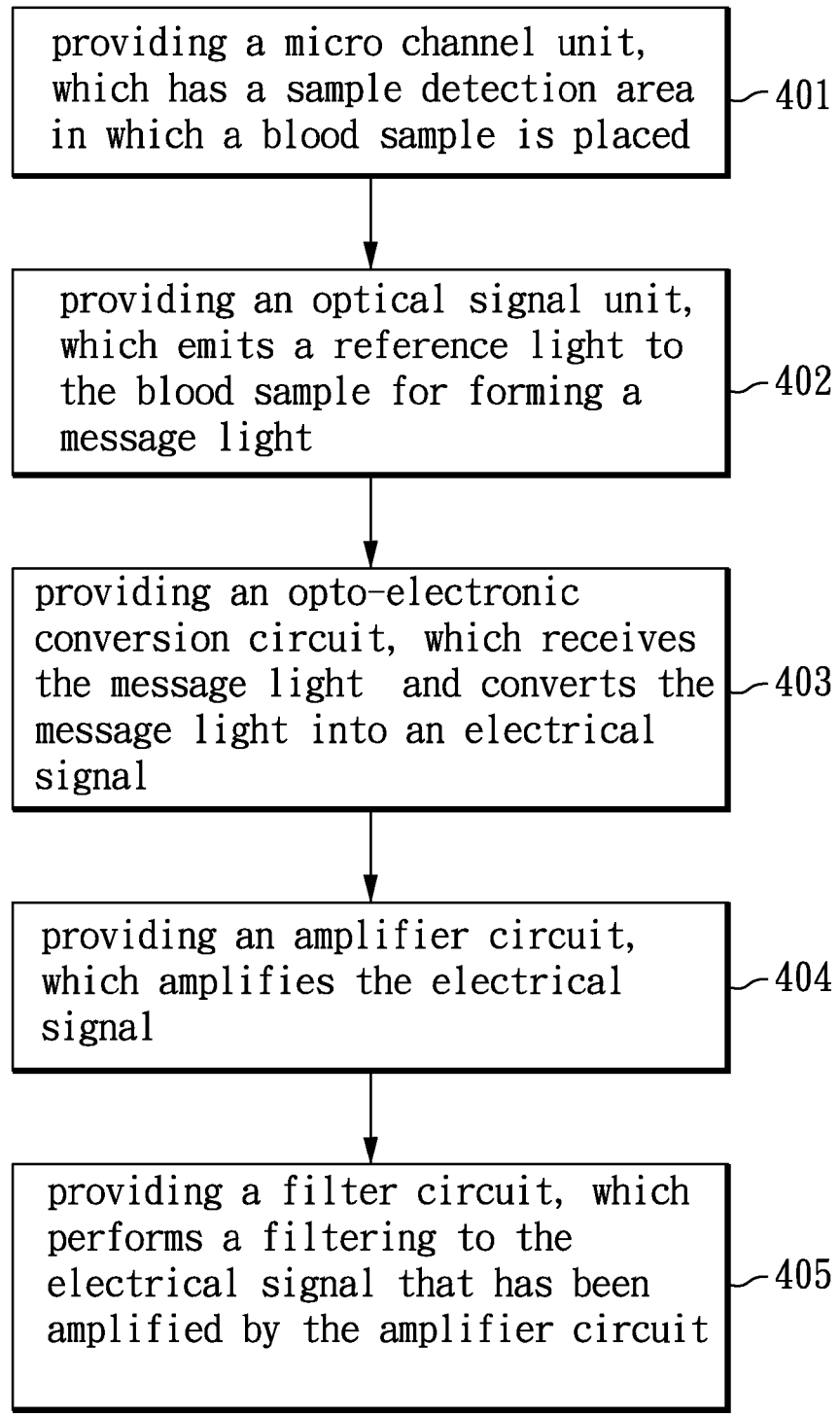
FIG. 5 is a flow chart for the blood coagulation detection method in accordance with a preferred embodiment of the present invention.

With reference to FIG. 5, there is shown a flow chart for the blood coagulation detection method in accordance with a preferred embodiment of the present invention. As shown in FIG. 5 as well as FIG. 1, the blood coagulation detection method of the present invention includes: providing a micro channel unit 101, which has a sample detection area 1011 in which a blood sample is placed (step 401); providing an optical signal unit 102, which emits a reference light 106 to the blood sample for forming a message light 107 (step 402); providing an opto-electronic conversion circuit 103, which receives the message light 107 and converts the message light into an electrical signal S (step 403); providing an amplifier circuit 104, which amplifies the electrical signal S (step 404); and providing a filter circuit 105, which performs a filtering to the electrical signal S that has been amplified by the amplifier circuit 104 (step 405).

It is noted that the operation of the blood coagulation detection method is similar to that of the blood coagulation detection device described previously, and thus a detailed description is deemed unnecessary.

The blood coagulation detection device and the blood coagulation detection method of the present invention can directly use whole blood for detection without having to generate plasma from the blood by centrifugal force, so as to reflect the actual status of the human blood. In addition, the volume of the blood coagulation detection device provided by the present invention is smaller than the prior detection device used in a hospital and can be manufactured at low cost, which can be easily carried to significantly increase the convenience of blood coagulation detection.

In view of the foregoing, it is known that, after being coagulated, the internal characteristic of blood is changed and thus the transparency degree is also changed. Thus, the change of transparency degree can be employed to determine when the blood begins to coagulate. However, the amount of change in transparency degree is extremely small. As a result, how to effectively determine the time of starting blood coagulation and how to process excessive external noises become the key points for achieving a better blood detection result. The blood coagulation detection device and the blood coagulation detection method of the present invention can utilize the back-end circuit architecture to obtain a better blood detection result.

Although the present invention has been explained in relation to its preferred embodiment, it is to be understood that many other possible modifications and variations can be made without departing from the spirit and scope of the invention as hereinafter claimed.

What is claimed is:

1. A blood coagulation detection device, comprising:
a micro channel unit having a sample detection area;
an optical signal unit for transmitting a reference light to the micro channel unit so as to form a message light;
an opto-electronic conversion circuit for receiving the message light and converting the message light into an electrical signal;
an amplifier circuit electrically connected to the opto-electronic conversion circuit for amplifying the electrical signal; and
a filter circuit electrically connected to the amplifier circuit for filtering the amplified electrical signal;
wherein the optical signal unit measures the blood coagulation by transmitting the reference light to the micro channel unit;
the filter circuit comprises a first filter circuit electrically connected to the amplifier circuit, and a second filter circuit electrically connected to the first filter circuit;
the first filter circuit is a notch filter; and
the central frequency of the notch filter is set to be 60 Hz.

2. The blood coagulation detection device as claimed in claim 1, wherein the optical signal unit includes a light emitting element and a light detecting element.

3. The blood coagulation detection device as claimed in claim 2, wherein the light emitting element is a light emitting diode and the light detecting element is a photoresistor.

4. The blood coagulation detection device as claimed in claim 3, wherein the light emitting diode is a green light emitting diode.

5. The blood coagulation detection device as claimed in claim 1, wherein the opto-electronic conversion circuit is a bridge circuit.

6. The blood coagulation detection device as claimed in claim 5, wherein the bridge circuit is a Wheatstone bridge or a Kelvin bridge.

7. The blood coagulation detection device as claimed in claim 1, wherein the second filter circuit is a fourth-order low pass filter.

8. The blood coagulation detection device as claimed in claim 7, wherein the fourth-order low pass filter has a cut-off frequency in the range of 20 Hz to 30 Hz.

9. The blood coagulation detection device as claimed in claim 7, wherein the fourth-order low pass filter is a Butterworth filter.

10. The blood coagulation detection device as claimed in claim 1, wherein the micro channel unit further includes a micro channel which is connected to the sample detection area.

11. The blood coagulation detection device as claimed in claim 1, wherein the sample detection area receives a blood sample.

12. The blood coagulation detection device as claimed in claim 11, wherein the blood sample is a whole blood sample.

13. The blood coagulation detection device as claimed in claim 1, wherein the amplifier circuit is an instrumentation amplifier.

14. The blood coagulation detection device as claimed in claim 1, wherein the second filter circuit has four first resistors and four second resistors, each of the first resistors is selected to have a same resistance value.

15. The blood coagulation detection device as claimed in claim 14, wherein the second filter circuit has four capacitors, each of the capacitors is selected to have a same capacitance value.

16. A blood coagulation detection method, comprising:
providing a micro channel unit, which has a sample detection area in which a blood sample is placed;
providing an optical signal unit, which emits a reference light to the blood sample for forming a message light;
providing an opto-electronic conversion circuit, which receives the message light and converts the message light into an electrical signal;
providing an amplifier circuit, which amplifies the electrical signal; and
providing a filter circuit, which performs a filtering to the electrical signal that has been amplified by the amplifier circuit;
wherein the optical signal unit measures the blood coagulation by transmitting the reference light to the micro channel unit;
the filter circuit includes a first filter circuit electrically connected to the amplifier circuit, and a second filter circuit electrically connected to the first filter circuit;
the first filter circuit is a notch filter; and
the central frequency of the notch filter is set to be 60 Hz.

17. The blood coagulation detection method as claimed in claim 16, wherein the optical signal unit includes a light emitting element and a light detecting element.

18. The blood coagulation detection method as claimed in claim 17, wherein the light emitting element is a light emitting diode and the light detecting element is a photoresistor.

19. The blood coagulation detection method as claimed in claim 16, wherein the opto-electronic conversion circuit is a bridge circuit.

20. The blood coagulation detection method as claimed in claim 16, wherein the second filter circuit has four first resistors and four second resistors, each of the first resistors is selected to have a same resistance value.

\* \* \* \* \*